(12) United States Patent
Nantel et al.

(10) Patent No.: US 7,932,228 B2
(45) Date of Patent: Apr. 26, 2011

(54) METHOD OF TREATING BONE OR PROSTATE CANCER WITH SELECTIVE BRADYKININ B1 RECEPTOR ANTAGONISTS

(75) Inventors: François Nantel, Sherbrooke (CA); Roger Chammas, Sao Paulo SP (BR); Pierre Sirois, Orford (CA); Bruno Joseph Battistini, Orford (CA)

(73) Assignee: Societe de Commercialisation des Produits de la Recherche Applique Socpra Sciences Sante et Humaines S.E.C., Quebec (CA)

( * ) Notice: Subject to any disclaimer, the term of this patent is extended or adjusted under 35 U.S.C. 154(b) by 821 days.

(21) Appl. No.: 11/451,142

(22) Filed: Jun. 12, 2006

(65) Prior Publication Data

US 2007/0015715 A1    Jan. 18, 2007

Related U.S. Application Data

(63) Continuation-in-part of application No. PCT/CA2005/001268, filed on Aug. 19, 2005.

(60) Provisional application No. 60/602,626, filed on Aug. 19, 2004, provisional application No. 60/689,058, filed on Jun. 10, 2005.

(51) Int. Cl.
*A61K 38/10* (2006.01)
*C07K 7/18* (2006.01)

(52) U.S. Cl. .................. 514/12.5; 530/314
(58) Field of Classification Search ............ 514/15; 530/328
See application file for complete search history.

(56) References Cited

U.S. PATENT DOCUMENTS

| | | | |
|---|---|---|---|
| 5,610,140 A | 3/1997 | Goodfellow et al. |
| 5,635,593 A | 6/1997 | Cheronis et al. |
| 5,700,779 A | 12/1997 | Goodfellow et al. |
| 5,750,506 A | 5/1998 | Goodfellow et al. |
| 5,834,431 A | 11/1998 | Stewart et al. |
| 5,843,900 A | 12/1998 | Cheronis et al. |
| 5,849,863 A | 12/1998 | Stewart et al. |
| 5,863,899 A | 1/1999 | Cheronis et al. |
| 5,935,932 A | 8/1999 | Stewart |
| 6,075,120 A | 6/2000 | Cheronis et al. |
| 7,041,785 B1 | 5/2006 | Regoli et al. |
| 7,211,566 B2 * | 5/2007 | Regoli et al. ............ 514/15 |
| 2004/0198666 A1 | 10/2004 | Regoli et al. |

FOREIGN PATENT DOCUMENTS

| | | |
|---|---|---|
| WO | 97/09346 A1 | 3/1997 |
| WO | 98/07746 A1 | 2/1998 |
| WO | 99/64039 A1 | 12/1999 |

OTHER PUBLICATIONS

Authier et al., Experimental Neurology, 2003, 182:12-20.
Calixto et al., Brit. J. Pharmacol., 2004, 143(7):803-818.
Gabra et al., European Journal of Pharmacology, 2002, 457:115-124.
Galoppini et al., Journal of Medicinal Chemistry, 1999, 42:409-414.
Gama Landgraf et al., Inflammation Research, 2004, 53:78-83.
Gaudreau et al., Canadian Journal of Physiology & Pharmacology, 1981, 59:371-379.
Gobeil et al., Br. J. Pharmacol., 1996, 118: 289-294.
Gobeil et al., Hypertension, 1999. 33:823-829.
Gobeil et al., Canadian Journal of Physiology & Pharmacology, 1997, 75:591-595.
Leeb-Lundberg et al., Pharmacological Reviews, 2005, 57:27-77.
MacNeil et al., Canadian Journal of Physiology & Pharmacology, 1997, 75:735-740.
Neugebauer et al., Canadian Journal of Physiology & Pharmacology, 2002, 80:287-292.
Ocean et al., Support Care Cancer, 2004, 12:619-625.
Stewart et al., Immunopharmacology, 1997, 36:167-172.
Stewart, Current Pharmacological Design, 2003, 9:2036-2042.
Taub et al., Cancer Research, 2003, 63:2037-2041.

* cited by examiner

*Primary Examiner* — Andrew D Kosar
(74) *Attorney, Agent, or Firm* — Nixon Peabody LLP

(57) ABSTRACT

Provided is a method for the use of a bradykinin B1 receptor antagonist of formula I: X-CO-Aaa$_0$-Aaa$_1$-Aaa$_2$-Aaa$_3$-Gly-α(Me)Phe-Ser-D-βNal-Aaa$_8$-OH (I) or a pharmaceutically acceptable salt or hydrate thereof wherein: X is $C_nH_{2n+1}$ or $C_iH_{2i}$—$C_6H_5$, where n is an integer from 1 to 3, and i is an integer from 0 to 3; Aaa$_0$ is Lys, Orn or Cit; Aaa$_1$ is Arg or Cit, and preferably Arg; Aaa$_2$ is Oic, Hyp or Pro, and preferably Oic; Aaa$_3$ is Pro or Oic, and preferably Pro; and Aaa$_8$ is Ile, Leu or Nle, and preferably Ile, for the treatment of metastases, cancers and/or chemotherapy-induced neuropathies, comprising the administration of the compound to a patient in need of such treatment. Also provided are compositions containing such antagonists and their thereof.

7 Claims, No Drawings

METHOD OF TREATING BONE OR PROSTATE CANCER WITH SELECTIVE BRADYKININ B1 RECEPTOR ANTAGONISTS

I. CROSS-RELATED APPLICATION

This application is a continuation-in-part of International Application No. PCT/CA2005/001268 filed Aug. 19, 2005, which designated the United States, and which claims the benefit of U.S. Provisional Application No. 60/602,626 filed Aug. 19, 2004 and the instant application also claims the benefit of U.S. Provisional 60/689,058 filed Jun. 10, 2005, the content of which are hereby incorporated by reference.

II. TECHNICAL FIELD

The present invention relates to the use of Bradykinin B1 receptor antagonist compounds for treating cancer and chemotherapy-induced neuropathy.

III. BACKGROUND OF THE INVENTION

Kinins, derived via the kallikrein-kinins pathway, have been demonstrated to affect the growth and metastasis of tumors through effects on cell growth and invasiveness. Four kinins (natural agonists) are responsible for the majority of bioactivities of this family of mediators. They include: bradykinin (BK), kallidin (KD or Lys-BK), desArg9 bradykinin (DBK) and desArg$^9$ kallidin (Lys-DBK). These kinins are known to activate two membrane-bound receptors which have been identified as the BKB1 (agonists: DBK and Lys-DBK) and the BKB2 (agonists: BK and Lys-BK) subtype (Leeb-Lundberg et al., Pharmacol. Rev. 57: 27-77, 2005).

```
BK              Arg Pro Pro Gly Phe Ser   (SEQ ID NO:1)
                Pro Phe Arg

Lys-BK          Lys Arg Pro Pro Gly Phe   (SEQ ID NO:2)
                Ser Pro Phe Arg desArg⁹BK       Arg Pro Pro Gly Phe Ser   (SEQ ID NO:3)
                Pro Phe Lys-desArg⁹BK Lys Arg Pro Pro Gly Phe     (SEQ ID NO:4)
                Ser Pro Phe
```

The BKB1 receptor (BKB1-R) subtype is not present under normal conditions, whereas the BKB2 receptor subtype (BKB2-R) is normally present on many cell types. Inducible BKB1-Rs are expressed in neurons, endothelial, smooth muscle and blood cells, and are involved in various types of inflammation, such as, but not limited to, asthma and arthritis, diabetes (type I and II-obesity) and various types of vasculopathies as well as central and peripheral neuropathies (pain) (Leeb-Lundberg et al., Pharmacol. Rev. 57: 27-77, 2005).

Peptidic BKB1-R antagonists have been described in the literature (Neugebauer et al., Can. J. Physiol. Pharmacol. 80: 287-292, 2002). Other peptidic BKB1-R antagonists have been disclosed in various published patent documents (WO97/09346, U.S. Pat. No. 6,075,120, U.S. Pat. No. 5,863, 899, U.S. Pat. No. 5,849,863, U.S. Pat. No. 5,843,900, U.S. Pat. No. 5,834,431, U.S. Pat. No. 5,750,506, U.S. Pat. No. 5,700,779, U.S. Pat. No. 5,635,593, U.S. Pat. No. 5,610,140, U.S. Ser. No. 09/242,751, WO98/07746). The antagonists used in this invention have been previously disclosed in U.S. Ser. No. 10/405,088.

Some cancers express, release and/or use peptides acting via autocrine/paracrine regulatory pathways to stimulate growth, angiogenesis and to modulate apoptosis. These cancers can also express the receptors activated by these peptides at the surface of many cells. Many other agents such as, but not limited to, Endothelins, Gastrin-releasing peptides, Ghrelin, Luteinizing Hormone-Releasing Hormone, Somatostatin, Vascular Endothelial Growth factor, have been identified as peptidic morphogens (phenotype modulators), growth regulators, pro-mitogens or growth factors.

A number of publications (reviewed by Stewart, Curr. Pharm. Des. 9: 2036-2042, 2003; Calixto et al., Brit. J. Pharmacol. 143: 803-818, 2005 and Leeb-Lundberg et al., Pharmacol. Rev. 57: 27-77, 2005) and patents (WO9964039; U.S. Pat. No. 5,849,863; U.S. Pat. No. 5,935,932) have alluded to the use of bradykinin antagonists as anti-cancer agents. However, the mechanisms of action of these compounds have not been clearly, even less fully, defined, as these compounds may be:

(i) anti-neoplastic (blocking basal and/or stimulated cell growth and proliferation);
(ii) anti-angiogenic (blocking the sprouting of new capillary blood vessels);
(iii) anti-migratory (blocking the invasiveness of cancer cells leading to metastasis);
(iv) and/or else.

Some of the proposed compounds may be unrelated to their ability to solely antagonize either BK receptors for these compounds are not specific BK receptor antagonists (Stewart et al., Immunopharmacology 36: 167-172, 1997).

Recent studies have reported that the BKB1-R subtype is expressed in a variety of tumors. Those include: prostate, renal, gastric and esophageal carcinomas. In addition, cancer cell lines such as PC-3, LNCaP and astrocytic tumor cells were also found to express the BKB1-R (Taub et al., Cancer Res. 63: 2037-2041, 2003; Calixto et al., Brit. J. Pharmacol. 143: 803-818, 2005; Leeb-Lundberg et al., Pharmacol. Rev. 57: 27-77, 2005).

Cell growth and proliferation of cancerous PC-3 cells in vitro was stimulated by a BKB1-R agonist (desArg$^9$-BK) and this growth was blocked by [Leu$^8$]desArg$^9$-BK, a BKB1-R antagonist (Taub et al., Cancer Res. 63: 2037-2041, 2003). However, basal growth and proliferation of PC-3, LNCaP and S-180 cells were not affected by BKB1-R antagonists (Taub et al., Cancer Res. 63: 2037-2041, 2003; Calixto et al., Brit. J. Pharmacol. 143: 803-818, 2005;).

Angiogenesis is another important aspect of cancer prognosis where the sprouting (formation and growth) of new capillary blood vessels within the tumor is a necessary step for tumor growth and invasiveness. Kinins are involved in the mechanisms of wound healing and angiogenesis and the two BK receptor subtypes appear to be implicated to various degrees. However, some studies suggest that the induced BKB1-R subtype is involved in the promotion of angiogenesis, whereas others propose that it is the constitutive BKB2-R subtype that is playing the major role (Stewart, Curr. Pharm. Des. 9: 2036-2042, 2003).

Another important aspect about the treatment of various forms of cancer and related conditions, is that anti-cancer chemotherapeutic agents are associated with complications such as the development of neuropathy, known as chemotherapy-induced neuropathy, which limit the dose and duration of anti-cancer treatments.

Depending on the antineoplastic substance used, the neuropathy can be (i) a pure sensory and painful neuropathy (caused by treatment with platinum-based compounds such as cisplatin, oxaliplatin, carboplatin, vinorelbine, gemcitabine, capecitabine)) or (ii) a mixed motor and sensory neuropathy that can involve and englobe the autonomic nervous system (caused by treatment with either taxanes (paclitaxel (=Taxol), docetaxel) or other agents (vinblastine, vincristine, vindesine, estramustine, suramin). Little is known about the mechanisms responsible for the development of neuropathy. Up to now, no drug is available to reliably prevent or cure chemotherapy-induced neuropathy (Ocean and Vahdat, Support Care cancer 12: 619-625, 2004).

BKB1-R antagonists have been reported to alleviate painful diabetic neuropathy (PDN) in various animal models of both Type I and Type II-obesity diabetes, nerve injury and other conditions, where BKB1-R are induced upon general inflammation (Leeb-Lundberg et al., Pharmacol. Rev. 57: 27-77, 2005).

The inventors formulated that kinins may mediate neuropathy through a direct action at induced BKB1-Rs and increase pain. These evidences suggest that blockade or antagonism of the actions of kinins may be useful for the treatment of chemotherapy-induced neuropathy of various etiologies and combinations.

IV. SUMMARY OF THE INVENTION

In accordance with the present invention, it was suggested that the presence (or addition) of kinins may increase tumor growth both through a direct action on cell growth and proliferation and indirectly through increased angiogenesis. Therefore, blockade or antagonism of the actions of kinins on kinin receptors involved in tumor growth and invasiveness may be useful for the treatment (reversibility), or prevention, of cancers such as breast cancer, ovarian cancer, cervical carcinoma, endometrial carcinoma, choriocarcinoma, soft tissue sarcomas, osteosarcomas, rhabdomyosarcomas, leiomyomas, leiomyosarcomas, head and neck cancers, lung and bronchogenic carcinomas, brain tumors, neuroblastomas, esophageal cancer, colorectal adenocarcinomas, bladder cancer, urothelial cancers, leukemia, lymphoma, malignant melanomas, oral squamous carcinoma, hepatoblastoma, glioblastoma, astrocytoma, medulloblastoma, Ewing's sarcoma, lipoma, liposarcoma, malignant fibroblast histoma, malignant Schwannoma, testicular cancers, thyroid cancers, Wilms' tumor, pancreatic cancers, colorectal adenocarcinoma, tongue carcinoma, gastric carcinoma, and nasopharyngeal cancers.

Accordingly, it is an object of the present invention to provide a new treatment modality against various forms of cancer in human patients. Another object of the present invention is to provide a treatment for cancer that utilizes a mechanism of action which is distinct and different from some other anti-cancer agents used. Still, a further object of the present invention is to alleviate autonomic and/or peripheral neuropathy resulting from the use of single and/or combinations of anti-carcinogenic or chemotherapeutic agents.

In accordance with the present invention, there is provided as a method of treating or preventing proliferation of cancer and/or chemotherapy-induced neuropathy, comprising administering to a mammalian patient in need of such treatment a bradykinin B1 receptor antagonist as represented by formula I:

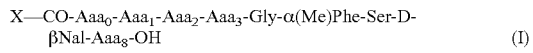

X—CO-Aaa$_0$-Aaa$_1$-Aaa$_2$-Aaa$_3$-Gly-α(Me)Phe-Ser-D-βNal-Aaa$_8$-OH    (I)

or a pharmaceutically acceptable salt or hydrate thereof wherein:

X is $C_nH_{2n+1}$ or $C_iH_{2i}$—$C_6H_5$, where n is an integer from 1 to 3, and i is an integer from 0 to 3;

Aaa$_0$ is Lys, Orn or Cit;
Aaa$_1$ is Arg or Cit, and preferably Arg;
Aaa$_2$ is Oic, Hyp or Pro, and preferably Oic;
Aaa$_3$ is Pro or Oic, and preferably Pro; and
Aaa$_8$ is Ile, Leu, Nle, and preferably Ile.

V. DETAILED DESCRIPTION OF THE PREFERRED EMBODIMENTS

In one aspect of the invention, the invention relates to a method of treating cancer comprising administering to a mammalian patient in need of such treatment a compound presented by formula I:

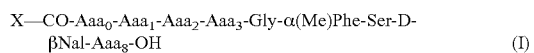

X—CO-Aaa$_0$-Aaa$_1$-Aaa$_2$-Aaa$_3$-Gly-α(Me)Phe-Ser-D-βNal-Aaa$_8$-OH    (I)

or a pharmaceutically acceptable salt or hydrate thereof wherein:

X is $C_nH_{2n+1}$ or $C_iH_{2i}$—$C_6H_5$, where n is an integer from 1 to 3, and i is an integer from 0 to 3;
Aaa$_0$ is Lys, Orn or Cit;
Aaa$_1$ is Arg or Cit, and preferably Arg;
Aaa$_2$ is Oic, Hyp or Pro, and preferably Oic;
Aaa$_3$ is Pro or Oic, and preferably Pro; and
Aaa$_8$ is Ile, Leu, Nle, and preferably Ile, Example of compounds that are useful in the method described herein are found below:

A) Ac-Orn[Oic$^2$,(α-Me)Phe$^5$,D-βNal$^7$,Ile$^8$]desArg$^9$BK;
B) Ac-Lys[Oic$^2$,(α-Me)Phe$^5$,D-βNal$^7$,Ile$^8$]desArg$^9$BK;
C) Ac-Orn[Oic$^2$,Oic$^3$,(α-Me)Phe$^5$,D-βNal$^7$,Ile$^8$]desArg$^9$BK;
D) Ac-Lys[Oic$^2$,Oic$^3$,(α-Me)Phe$^5$,D-βNal$^7$,Ile$^8$]desArg$^9$BK;
E) Propanoyl-Orn[Oic$^2$,(α-Me)Phe$^5$,D-βNal$^7$,Ile$^8$]desArg$^9$BK;
F) Propanoyl-Lys[Oic$^2$,(α-Me)Phe$^5$,D-βNal$^7$,Ile$^8$]desArg$^9$BK;
G) Propanoyl-Orn[Oic$^2$,Oic$^3$,(α-Me)Phe$^5$,D-βNal$^7$,Ile$^8$]desArg$^9$BK;
H) Propanoyl-Lys[Oic$^2$,Oic$^3$,(α-Me)Phe$^5$,D-βNal$^7$,Ile$^8$]desArg$^9$BK;
I) Butanoyl-Orn[Oic$^2$,(α-Me)Phe$^5$,D-βNal$^7$,Ile$^8$]desArg$^9$BK;
J) Butanoyl-Lys[Oic$^2$,(α-Me)Phe$^5$,D-βNal$^7$,Ile$^8$]desArg$^9$BK;
K) Butanoyl-Orn[Oic$^2$,Oic$^3$,(α-Me)Phe$^5$,D-βNal$^7$,Ile$^8$]desArg$^9$BK;
L) Butanoyl-Lys[Oic$^2$,Oic$^3$,(α-Me)Phe$^5$,D-βNal$^7$,Ile$^8$]desArg$^9$BK;
M) Bz-Orn[Oic$^2$,(α-Me)Phe$^5$,D-βNal$^7$,Ile$^8$]desArg$^9$BK;
N) Bz-Lys[Oic$^2$,(α-Me)Phe$^5$,D-βNal$^7$,Ile$^8$]desArg$^9$BK;
O) Bz-Orn[Oic$^2$,Oic$^3$,(α-Me)Phe$^5$,D-βNal$^7$,Ile$^8$]desArg$^9$BK;
P) Bz-Lys[Oic$^2$,Oic$^3$,(α-Me)Phe$^5$,D-βNal$^7$,Ile$^8$]desArg$^9$BK;
Q) 2-phenyl-acetyl-Orn[Oic$^2$,(α-Me)Phe$^5$,D-βNal$^7$,Ile$^8$]desArg$^9$BK;
R) 2-phenyl-acetyl-Lys[Oic$^2$,(α-Me)Phe$^5$,D-βNal$^7$,Ile$^8$]desArg$^9$BK;
S) 2-phenyl-acetyl-Orn[Oic$^2$,Oic$^3$,(α-Me)Phe$^5$,D-βNal$^7$,Ile$^8$]desArg$^9$BK;
T) 2-phenyl-acetyl-Lys[Oic$^2$,Oic$^3$,(α-Me)Phe$^5$,D-βNal$^7$,Ile$^8$]desArg$^9$BK;
U) 3-phenyl-propanoyl-Orn[Oic$^2$,(α-Me)Phe$^5$,D-βNal$^7$,Ile$^8$]desArg$^9$BK;
V) 3-phenyl-propanoyl-Lys[Oic$^2$,(α-Me)Phe$^5$,D-βNal$^7$,Ile$^8$]desArg$^9$BK;

W) 3-phenyl-propanoyl-Orn[Oic$^2$,Oic$^3$,(α-Me)Phe$^5$,D-βNal$^7$,Ile$^8$]desArg$^9$BK;
X) 3-phenyl-propanoyl-Lys[Oic$^2$,Oic$^3$,(α-Me)Phe$^5$,D-βNal$^7$,Ile$^8$]desArg$^9$BK;
Y) 4-phenyl-butanoyl-Orn[Oic$^2$,(α-Me)Phe$^5$,D-βNal$^7$,Ile$^8$]desArg$^9$BK;
Z) 4-phenyl-butanoyl-Lys[Oic$^2$,(α-Me)Phe$^5$,D-βNal$^7$,Ile$^8$]desArg$^9$BK;
AA) 4-phenyl-butanoyl-Orn[Oic$^2$,Oic$^3$,(α-Me)Phe$^5$,D-βNal$^7$,Ile$^8$]desArg$^9$BK; and
BB) 4-phenyl-butanoyl-Lys[Oic$^2$,Oic$^3$,(α-Me)Phe$^5$,D-βNal$^7$,Ile$^8$]desArg$^9$BK;

Another embodiment of the invention is a method of treating cancer comprising administering to a mammalian patient in need of such treatment a compound of formula I in an amount that is effective for treating cancer, wherein the compound is co-administered with one or more other agents or ingredients, such as, but not limited to, anti-cancer, synergists, stabilizing substances, antineoplastic agents and cytostatic (chemotherapy) agents such as, but not limited to, taxane and platinum compounds.

Another embodiment of the invention is a method of preventing, alleviating, treating chemotherapy-induced neuropathy comprising administering to a mammalian patient in need of such treatment a compound of formula I in an amount that is effective for treating chemotherapy-induced neuropathy, wherein the compound is co-administered with one or more other agents or ingredients, such as, but not limited to, anti-cancer, synergists, stabilizing substances, antineoplastic agents and cytostatic (chemotherapy) agents such as, but not limited to, taxane and platinum compounds.

Another embodiment of the invention is a pharmaceutical composition comprised of a compound of formula I in combination with at least one member selected from the group consisting of, but not limited to, anti-cancer, synergists, stabilizing substances, antineoplastic agents and cytostatic (chemotherapy) agents such as, but not limited to, taxane and platinum compounds, for the treatment of cancers.

The magnitude of a prophylactic or therapeutic dose of a compound of formula I will, of course, vary with the nature and the severity of the condition to be treated and with the particular compound of formula I and its route of administration.

The magnitude of a prophylactic or therapeutic dose of a compound of formula I will also vary according to a variety of factors including the age, weight, general health, sex, diet, time of administration, rate of excretion, drug combination and response of the individual patient. In general, the daily dose will range from about 0.001 mg to about 100 mg per kg body weight of a mammal, preferably about 0.01 mg to about 10 mg per kg. Dosages outside these limits may be used in some severe cases where the benefits (survival and pain reduction) out weights the treatment side-effects.

The amount of active ingredient that may be combined with the carrier materials to produce a single dosage form will vary depending upon the host treated and the particular mode of administration. For example, a formulation intended for the oral administration of humans may contain from about 0.5 mg to 5 g of active agent compounded with an appropriate and convenient amount of carrier material which may vary from about 5 to about 95 percent of the total composition. Dosage unit forms will generally contain between from about 1 mg to about 2 g of an active ingredient, typically 25 mg, 50 mg, 100 mg, 200 mg, 300 mg, 400 mg, 500 mg, 600 mg, 800 mg or 1000 mg.

For use in the treatment or prophylaxis of cancer, the compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as, but not limited to, mice, rats, cats, dogs, sheep, cattle, horses, the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Co-solvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, co-solvent, emulsifier, penetration enhancer, preservative system, and emollient.

The ability of the compounds of formula I to interact with the bradykinin B1 receptor makes them useful for preventing or reversing undesirable events caused by bradykinins in a mammalian, especially human subject. This mimicking or antagonism of the actions of bradykinin at the BKB1-R indicates that the compounds and pharmaceutical compositions thereof are useful to treat, prevent, or ameliorate the signs and symptoms of cancer, chemotherapy-induced neuropathy and related disorders in mammals and especially in humans.

Methods of Synthesis

All compounds were synthesized with an Applied Biosystems 430, a peptide synthesizer using Merrifield type resins with the first amino acid attached. Amino acids were activated by dicyclohexylcarbodiimide/1-hydroxybenzotriazole (Peptides International, Louisville, Ky.) in 1-methyl-2 pyrrolidinone. Peptides were cleaved from the resins with anhydrous hydrogen fluoride in the presence of appropriate scavengers. The resulting peptides were purified by medium pressure reversed-phase ($C_{18}$) chromatography and if necessary by high performance liquid chromatography (HPLC). Peptide purity was assessed by analytical HPLC and identity confirmed by ion-spray mass spectrometry (VG Quattro, Manchester, UK).

N-acylation of peptides was performed on the solid phase with acetyl anhydrides or other acyl chlorides.

Effectiveness for the compounds A to BB listed above in cancer and in chemotherapy-induced neuropathy is demonstrated hereinafter.

In Vitro Bioassays to Assess the Selectivity to BK Receptor Subtype (Isolated Preparations in Organ Baths)

Selected antagonists were tested for activities in three isolated organs: (1) the rabbit aorta (rbA), (2) the human umbilical vein (hUV) and (3) the rabbit jugular vein (rbJV). All details regarding the procurements of human umbilical cords and rabbit vessels as well as, the procedures for preparing the isolated organs and the experimental protocols are described in these respective publications: rbA (Neugebauer et al., Can. J. Physiol. Pharmacol. 80: 287-292, 2002); hUV (Gobeil et al., Br. J. Pharmacol. 118: 289-294, 1996), and rbJV (Gaudreau et al., Can. J. Physiol. Pharmacol. 59: 371-379, 1981). The rabbit aorta without endothelium (which contains only the BKB1-R) was used to determine the antagonistic activities of each compound.

In human, the hUV that contains BKB1 and BKB2-Rs was treated with HOE 140, a BKB2-R antagonist, to eliminate the interference of the BKB2-R in experiments intended to measure the antagonistic activity of each compound in BKB1-R challenged with Lys-desArg$^9$BK. The rabbit jugular vein (a pure BKB2-R system) was used to exclude any action of the new compounds on the BKB2-R and thus establish their selectivity. All tissues were treated with captopril (1 µM) to prevent the degradation of the peptidic agonists. Repeated applications of a single and double concentration of BK (on rbJV,) or of desArg$^9$BK (rbA and hUV) were made in the absence and in presence of the various peptides to evaluate their apparent affinities as antagonists. The antagonists were applied 10 min before measuring the myotropic effects of either BK (the BKB2-R agonist) or Lys-desArg$^9$BK (the BKB1-R agonist). All kinin antagonists were initially applied to tissues at concentration of 10 µg/mL to measure their "potential agonistic activities, ($\alpha^E$)" in comparison with BK (in the BKB2-R preparation) or Lys-desArg$^9$BK (in the BKB1-R preparations).

The invention is illustrated in connection with the following examples, which are given to illustrate the invention rather than to limit its scope. All the end products of the formula I were analyzed by HPLC, mass spectrometry and nuclear magnetic resonance.

Example I

The potential of a BKB1-R antagonist to inhibit tumor progression in an orthoptic prostate cancer rat model was evaluated. Under anesthesia, male Copenhagen rats were injected in the anterior prostatic lobe with 100 000 MAT-LyLu-B2 prostate cancer cells. One day after the surgery, the animals received a daily injection of either saline or Compound A (3 mg/kg s.c.). At 21 days after the surgery, the animals were sacrificed and the prostate tumor was excised and weighted. Average weight of the prostate and tumor was 1856±443 mg for saline-treated rats and 504±135 mg with Compound A-treated animals (n=5-6 p<0.05). Two other cancerous cell-types (R 3327-G, MAT-Lu) were implanted in rats and similar results were obtained at inhibiting tumor progression dose-dependently over periods of time. A BKB1-Ra was also reported effective at stopping and reversing the progression of established tumor, considering efficacy, reversibility and relapse of treatment. These elements were maintained upon dual and triple combinations with other anti-cancer, anti-angiogenic, anti-proliferative agents such as taxane and platinum related compounds.

Example II

The potential of a BKB1-R antagonist to limit the progression of bone metastasis in an animal model was evaluated. Under anesthesia, male Copenhagen rats were implanted with an arterial catheter. MAT-Lu cancer cells (50,000 cells) were then infused through the catheter. One day after the infusion, the animals received a daily injection of either saline or Compound A (0.3-3 mg/kg s.c.). The primary endpoint of the study was the time to hind leg paralysis through spinal metastasis which usually occurs within 21 days following metastasis to the lumbar vertebra. A BKB1-Ra was reported effective at prolonging the time to hind leg paralysis and reducing the extent of metastasis.

Example III

The potential of a BKB1-R antagonist to prevent and limit the progression or reversed established chemotherapy-induced neuropathy in animal models of pain/hyperalgesia was evaluated. Sprague-Dawley rats were treated for three weeks with either cisplatin (2 mg/kg i.p. every 3 days) or paclitaxel (5 mg/kg i.v. once weekly). Compound A (0.3-3 mg/kg s.c. qd) was administered either at the initiation of the chemotherapy or after two weeks of treatment when signs of neuropathy were detectable. Nociception was evaluated using the spinal tail immersion thermal cold-test and the mechanical (paw pressure-allodynia) test.

For the tail-immersion test, the rat was gently wrapped in a towel and held at a 45° angle to an ice-water bath set at 4±1° C. The latency between submersion of the tail and its removal from the water by the animal was recorded, with a maximum cut-off time of 15 seconds (Authier et al., Exp. Neurol. 182: 12-20, 2003). Rats were habituated to the testing procedures and to the handling by the investigator during the week before the experiment.

The paw pressure test was carried out as described in (Authier et al., Exp. Neurol. 182: 12-20, 2003). Nociceptive thresholds, expressed in grams, were measured by applying increasing pressure to the right hind paw using an Ugo Basile analgesimeter. The parameter used to quantify the nociceptive threshold was the vocalization of the animal. Rats were accustomed to the testing procedures and handling by the investigator during the week before the experiment. Experiments were performed until two consecutive pressure values were obtained. The cutoff pressure was 450 g.

In both tests, pre-treatment latencies were determined 3 times with an interval of 24 h starting 3 days before the initiation of chemotherapy and the mean was calculated in order to obtain stable pre-drug response latencies. Following the administration of Compound A, the effects were determined at different time interval.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. A method for the treatment of bone or prostate cancer comprising the administration to a patient in need of such a treatment a compound of formula I:

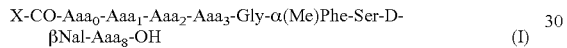

or a pharmaceutically acceptable salt or hydrate thereof wherein:

X is $C_nH_{2n+1}$ or $C_iH_{2i}$—$C_6H_5$, where n is an integer from 1 to 3, and i is an integer from 0 to 3;
$Aaa_0$ is Lys, Orn or Cit;
$Aaa_1$ is Arg or Cit;
$Aaa_2$ is Oic, Hyp or Pro;
$Aaa_3$ is Pro or Oic; and
$Aaa_8$ is Ile, Leu or Nle.

2. The method of claim 1 wherein said patient is a mammal.

3. The method of claim 1 wherein the treatment of cancer comprises increasing the survival of the patient.

4. The method of claim 1 wherein treatment of cancer comprises either reducing tumor progression, reducing tumor size, or both.

5. The method of claim 1 wherein the compound of formula I is co-administered with an anticancer agent.

6. The method of claim 5 wherein the anticancer agent is selected from the group consisting of synergists, stabilizing substances, antineoplastic agents and cytostatic agents.

7. The method according to claim 1 wherein said compound of formula I is one of the following compounds or a pharmaceutically acceptable salt or hydrate thereof:

A) Ac-Orn[$Oic^2$,($\alpha$-Me)$Phe^5$,D-$\beta Nal^7$,$Ile^8$]des$Arg^9$BK;
B) Ac-Lys[$Oic^2$,($\alpha$-Me)$Phe^5$,D-$\beta Nal^7$,$Ile^8$]des$Arg^9$BK;
C) Ac-Orn[$Oic^2$,$Oic^3$,($\alpha$-Me)$Phe^5$,D-$\beta Nal^7$,$Ile^8$]des$Arg^9$BK;
D) Ac-Lys[$Oic^2$,$Oic^3$,($\alpha$-Me)$Phe^5$,D-$\beta Nal^7$,$Ile^8$]des$Arg^9$BK;
E) Propanoyl-Orn[$Oic^2$,($\alpha$-Me)$Phe^5$,D-$\beta Nal^7$,$Ile^8$]des$Arg^9$BK;
F) Propanoyl-Lys[$Oic^2$,($\alpha$-Me)$Phe^5$,D-$\beta Nal^7$,$Ile^8$]des$Arg^9$BK;
G) Propanoyl-Orn[$Oic^2$,$Oic^3$,($\alpha$-Me)$Phe^5$,D-$\beta Nal^7$,$Ile^8$]des$Arg^9$BK;
H) Propanoyl-Lys[$Oic^2$,$Oic^3$,($\alpha$-Me)$Phe^5$,D-$\beta Nal^7$,$Ile^8$]des$Arg^9$BK;
I) Butanoyl-Orn[$Oic^2$,($\alpha$-Me)$Phe^5$,D-$\beta Nal^7$,$Ile^8$]des$Arg^9$BK;
J) Butanoyl-Lys[$Oic^2$,($\alpha$-Me)$Phe^5$,D-$\beta Nal^7$,$Ile^8$]des$Arg^9$BK;
K) Butanoyl-Orn[$Oic^2$,$Oic^3$,($\alpha$-Me)$Phe^5$,D-$\beta Nal^7$,$Ile^8$]des$Arg^9$BK;
L) Butanoyl-Lys[$Oic^2$,$Oic^3$,($\alpha$-Me)$Phe^5$,D-$\beta Nal^7$,$Ile^8$]des$Arg^9$BK;
M) Bz-Orn[$Oic^2$,($\alpha$-Me)$Phe^5$,D-$\beta Nal^7$,$Ile^8$]des$Arg^9$BK;
N) Bz-Lys[$Oic^2$,($\alpha$-Me)$Phe^5$,D-$\beta Nal^7$,$Ile^8$]des$Arg^9$BK;
O) Bz-Orn[$Oic^2$,$Oic^3$,($\alpha$-Me)$Phe^5$,D-$\beta Nal^7$,$Ile^8$]des$Arg^9$BK;
P) Bz-Lys[$Oic^2$,$Oic^3$,($\alpha$-Me)$Phe^5$,D-$\beta Nal^7$,$Ile^8$]des$Arg^9$BK;
Q) 2-phenyl-acetyl-Orn[$Oic^2$,($\alpha$-Me)$Phe^5$,D-$\beta Nal^7$,$Ile^8$]des$Arg^9$BK;
R) 2-phenyl-acetyl-Lys[$Oic^2$,($\alpha$-Me)$Phe^5$,D-$\beta Nal^7$,$Ile^8$]des$Arg^9$BK;
S) 2-phenyl-acetyl-Orn[$Oic^2$,$Oic^3$,($\alpha$-Me)$Phe^5$,D-$\beta Nal^7$,$Ile^8$]des$Arg^9$BK;
T) 2-phenyl-acetyl-Lys[$Oic^2$,$Oic^3$,($\alpha$-Me)$Phe^5$,D-$\beta Nal^7$,$Ile^8$]des$Arg^9$BK;
U) 3-phenyl-propanoyl-Orn[$Oic^2$,($\alpha$-Me)$Phe^5$,D-$\beta Nal^7$,$Ile^8$]des$Arg^9$BK;
V) 3-phenyl-propanoyl-Lys[$Oic^2$,($\alpha$-Me)$Phe^5$,D-$\beta Nal^7$,$Ile^8$]des$Arg^9$BK;
W) 3-phenyl-propanoyl-Orn[$Oic^2$,$Oic^3$,($\alpha$-Me)$Phe^5$,D-$\beta Nal^7$,$Ile^8$]des$Arg^9$BK;
X) 3-phenyl-propanoyl-Lys[$Oic^2$,$Oic^3$,($\alpha$-Me)$Phe^5$,D-$\beta Nal^7$,$Ile^8$]des$Arg^9$BK;
Y) 4-phenyl-butanoyl-Orn[$Oic^2$,($\alpha$-Me)$Phe^5$,D-$\beta Nal^7$,$Ile^8$]des$Arg^9$BK;
Z) 4-phenyl-butanoyl-Lys[$Oic^2$,($\alpha$-Me)$Phe^5$,D-$\beta Nal^7$,$Ile^8$]des$Arg^9$BK;
AA) 4-phenyl-butanoyl-Orn[$Oic^2$,$Oic^3$,($\alpha$-Me)$Phe^5$,D-$\beta Nal^7$,$Ile^8$]des$Arg^9$BK; and
BB) 4-phenyl-butanoyl-Lys[$Oic^2$,$Oic^3$,($\alpha$-Me)$Phe^5$,D-$\beta Nal^7$,$Ile^8$]des$Arg^9$BK.

* * * * *

SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Bradykinin (BK)

<400> SEQUENCE: 1

Arg Pro Pro Gly Phe Ser Pro Phe Arg
1               5

<210> SEQ ID NO 2
<211> LENGTH: 10
<212> TYPE: PRT
<213> ORGANISM: Artificial Sequence
<220> FEATURE:
<223> OTHER INFORMATION: Lys-BK

<400> SEQUENCE: 2

Lys Arg Pro Pro Gly Phe Ser Pro Phe Arg
1               5                   10

```
<210> SEQ ID NO 3
<211> LENGTH: 8
<212> TYPE: PRT
<213> ORGANISM: Artificial Sequence
<220> FEATURE:
<223> OTHER INFORMATION: desArg9 BK

<400> SEQUENCE: 3

Arg Pro Pro Gly Phe Ser Pro Phe
 1               5

<210> SEQ ID NO 4
<211> LENGTH: 9
<212> TYPE: PRT
<213> ORGANISM: Artificial Sequence
<220> FEATURE:
<223> OTHER INFORMATION: Lys-desArg9 BK

<400> SEQUENCE: 4

Lys Arg Pro Pro Gly Phe Ser Pro Phe
 1               5
```